US010420714B2

(12) United States Patent
Comeron et al.

(10) Patent No.: US 10,420,714 B2
(45) Date of Patent: Sep. 24, 2019

(54) FOAMING COSMETIC COMPOSITIONS AND METHODS FOR PRODUCING THE SAME

(71) Applicant: L'OREAL, Paris (FR)

(72) Inventors: Vanessa Comeron, Roselle Park, NJ (US); Aziza Suleiman, Paterson, NJ (US); Anand Mahadeshwar, Scotch Plains, NJ (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 15/282,812

(22) Filed: Sep. 30, 2016

(65) Prior Publication Data
US 2018/0092814 A1    Apr. 5, 2018

(51) Int. Cl.
| | | |
|---|---|---|
| *A61K 8/41* | (2006.01) | |
| *A61K 8/44* | (2006.01) | |
| *A61K 8/45* | (2006.01) | |
| *A61K 8/73* | (2006.01) | |
| *A61Q 19/00* | (2006.01) | |
| *A61K 8/81* | (2006.01) | |
| *A61K 8/898* | (2006.01) | |
| *A61K 8/04* | (2006.01) | |
| *A61K 8/19* | (2006.01) | |
| *A61K 8/87* | (2006.01) | |
| *A61K 8/894* | (2006.01) | |
| *A61K 8/31* | (2006.01) | |
| *A61K 8/34* | (2006.01) | |
| *A61K 8/49* | (2006.01) | |
| *A61Q 5/00* | (2006.01) | |

(52) U.S. Cl.
CPC .............. *A61K 8/046* (2013.01); *A61K 8/19* (2013.01); *A61K 8/31* (2013.01); *A61K 8/345* (2013.01); *A61K 8/41* (2013.01); *A61K 8/44* (2013.01); *A61K 8/442* (2013.01); *A61K 8/45* (2013.01); *A61K 8/4993* (2013.01); *A61K 8/737* (2013.01); *A61K 8/8141* (2013.01); *A61K 8/8152* (2013.01); *A61K 8/87* (2013.01); *A61K 8/894* (2013.01); *A61K 8/898* (2013.01); *A61Q 5/00* (2013.01); *A61Q 19/00* (2013.01); *A61K 2800/10* (2013.01); *A61K 2800/22* (2013.01); *A61K 2800/48* (2013.01); *A61K 2800/52* (2013.01); *A61K 2800/5424* (2013.01); *A61K 2800/594* (2013.01)

(58) Field of Classification Search
None
See application file for complete search history.

(56) References Cited

U.S. PATENT DOCUMENTS

| | | | |
|---|---|---|---|
| 3,110,695 A | 11/1963 | Ceresa | |
| 3,304,273 A | 2/1967 | Stamberger | |
| 3,383,351 A | 5/1968 | Stamberger | |
| 3,412,054 A | 11/1968 | Milligan et al. | |
| 3,523,095 A | 8/1970 | Laurito et al. | |
| 4,301,601 A | 11/1981 | Carr | |
| 4,874,604 A | 10/1989 | Sramek | |
| 5,902,225 A | 5/1999 | Monson | |
| 5,985,295 A | 11/1999 | Peffly | |
| 6,649,173 B1 | 11/2003 | Arnaud et al. | |
| 6,726,916 B1 | 4/2004 | Ramin | |
| 2004/0253297 A1 | 12/2004 | Hedges et al. | |
| 2004/0258628 A1 | 12/2004 | Riedel et al. | |
| 2006/0078520 A1 | 4/2006 | Pays et al. | |
| 2008/0280797 A1 | 11/2008 | Compain | |
| 2013/0108557 A1 | 5/2013 | Abram et al. | |
| 2013/0287724 A1 | 10/2013 | Hoffman et al. | |
| 2014/0105945 A1 | 4/2014 | Bui et al. | |
| 2015/0004114 A1* | 1/2015 | Tan .......................... | A61K 8/87 424/70.13 |
| 2015/0004116 A1 | 1/2015 | Tan et al. | |
| 2015/0004119 A1 | 1/2015 | Tan et al. | |
| 2015/0004121 A1 | 1/2015 | Tan et al. | |
| 2015/0150772 A1 | 6/2015 | Krueger et al. | |
| 2016/0030307 A1 | 2/2016 | Chen et al. | |
| 2016/0175206 A1 | 6/2016 | Tan et al. | |
| 2016/0175237 A1 | 6/2016 | Shin et al. | |
| 2016/0184195 A1 | 6/2016 | Tan et al. | |

FOREIGN PATENT DOCUMENTS

| | | | |
|---|---|---|---|
| DE | 1152536 | | 8/1963 |
| EP | 0216479 A1 | | 4/1987 |
| EP | 0847752 A1 | | 6/1998 |
| EP | 0898958 A1 | | 3/1999 |
| EP | 0898960 A1 | | 3/1999 |
| FR | 2812543 A | | 2/2002 |
| GB | 1040452 A | | 8/1966 |
| WO | WO 2013/064596 | * | 5/2013 |
| WO | WO 2014/144076 | * | 9/2014 |

(Continued)

OTHER PUBLICATIONS

English language Abstract for EP 0898960A1, dated Mar. 3, 1999.
Co-pending U.S. Appl. No. 15/282,952, "Compositions and Methods for Treating Hair," Inventors: Vanessa Comeron et al., filed Sep. 30, 2016.
Co-pending U.S. Appl. No. 15/282,502, "Compositions and Methods for Treating Hair," Inventors: Vanessa Comeron et al., filed Sep. 30, 2016.
Co-pending U.S. Appl. No. 15/282,480, "Compositions and Methods for Treating Hair," Inventors: Vanessa Comeron et al., filed Sep. 30, 2016.

(Continued)

*Primary Examiner* — Brian Gulledge
(74) *Attorney, Agent, or Firm* — The Marbury Law Group, PLLC

(57) ABSTRACT

Disclosed herein are foaming cosmetic compositions comprising: at least one anionic thickening agent; at least two alkaline compounds; and at least one silicone. Methods for producing the foaming cosmetic compositions and for improving the stability of a foamed cosmetic composition are also disclosed.

19 Claims, 2 Drawing Sheets

(56) References Cited

FOREIGN PATENT DOCUMENTS

| WO | 2014/210480 A1 | 12/2014 |
|---|---|---|
| WO | 2016/100885 A1 | 6/2016 |
| WO | 2017/165931 A1 | 10/2017 |

OTHER PUBLICATIONS http://www.gnpd.com. Mintel—Wave Aid, XP002776284, retrieved from Internet Jul. 2016.
http://www.gnpd.com. Mintel—XXL Body Ultra Strong Thickening Mousse, XP002776283, retrieved from Internet Oct. 2012.
Invitation to Pay Additional Fees for copending Application No. PCT/EP2017/054356, dated Jan. 9, 2018.
International Search Report for counterpart Application No. PCT/US2017/054791, dated Dec. 12, 2017.
Non-Final Office Action for copending U.S. Appl. No. 15/282,502, dated Aug. 21, 2017.
Non-Final Office Action for copending U.S. Appl. No. 15/282,952, dated Oct. 6, 2017.
Non-Final Office Action for copending U.S. Appl. No. 15/282,480, dated Feb. 5, 2018.
International Search Report and Written Opinion for counterpart Application No. PCT/US2017/054364, dated Nov. 29, 2017.
International Search Report and Written Opinion for counterpart Application No. PCT/US2017/054791, dated Feb. 12, 2018.
Final Office Action for copending U.S. Appl. No. 15/1282,952, dated Mar. 9, 2018.
Comparatively Speaking: Fatty Alcohols vs. Fatty Acids vs. Esters: retrieved from internet: http://www.cosmeticsandtoiletries.com/research/chemistry/97861099.html. Retrieved on Aug. 16, 2017.
Fatty Acids, alcohols and esters: retrieved from Internet: http://thenakedchemist.com/fatty-acids-alcohols-and-esthers/. Retrieved on Aug. 16, 2017.
Wacker Silicones, "Beisil ADM 8301 E," 2013, pp. 1-2.
Clarient, "SilCare Silicone SEA," 2004, pp. 1-2.
International Search Report and Written Opinion for counterpart Application No. PCT/US2017/054356, dated Mar. 15, 2018.
Final Office Action for copending U.S. Appl. No. 15/1282,502, dated Apr. 10, 2018.
Notice of Allowance for copending U.S. Appl. No. 15/282,952, dated Aug. 30, 2018.
Non-Final Office Action for copending U.S. Appl. No. 15/282,502, dated Sep. 18, 2018.
Final Office Action for co-pending U.S. Appl. No. 15/282,480, dated Feb. 6, 2019.
Non-Final Office Action for copending U.S. Appl. No. 15/282,480, dated Aug. 16, 2018.
Final Office Action for co-pending U.S. Appl. No. 15/282,502, dated May 6, 2019.
International Preliminary Report on Patentability for counterpart Application No. PCT/US2017/054791, dated Apr. 11, 2019.
International Preliminary Report on Patentability for counterpart Application No. PCT/US2017/054364, dated Apr. 11, 2019.
International Preliminary report on Patentability for counterpart Application No. PCT/US2017/054356, dated Apr. 11, 2019.

\* cited by examiner

FOAMING COSMETIC COMPOSITIONS AND METHODS FOR PRODUCING THE SAME

FIELD OF THE INVENTION

The disclosure relates to foam cosmetic compositions, in particular, compositions comprising at least one anionic thickener and at least two different bases for neutralization, and to methods of producing said compositions.

BACKGROUND

Many cosmetic compositions are in the form of a foam or mousse. The introduction of a gas into a cosmetic composition to give it a light texture and the appearance of a foam is known as overrunning.

Such cosmetic compositions in the form of a foam are either aerosol products distributed from a pressurized container, with the aid of a propellant and thus forming a foam, or products distributed from a container using a mechanical pump connected to a distribution head, without an aid of propellant. However, foam compositions currently available are not always entirely satisfactory in terms of foam quality, foam durability, and/or foam stability.

Cosmetic compositions often include silicones or oils to improve the texture and/or feel of the composition, ease of application, spreadability, and/or cosmeticity of the composition.

An aerosol foam composition typically comprises a cosmetic composition in a liquid form packaged with a volatile liquid, i.e., a propellant dissolved or finely and uniformly dispersed in the composition. The aerosol is dispensed from the container into a foam.

A conventional aerosol foam cosmetic composition can be roughly classified into an aqueous foam cosmetic composition and an oily foam cosmetic composition. Oil and/or silicone components are usually incorporated in order to improve wear, to provide emollient properties, and to help disperse hydrophobic powders in the foam cosmetic composition. However, large amounts of an oil and/or silicone component, for example heavy silicones or oils, can adversely affect the foam quality, stability, and/or durability. In addition, the presence of oil and/or silicone components has a disadvantage that the aerosol foam cosmetic composition can be too sticky and/or too oily and does not give fresh or watery feeling.

Stability of a foam can be critical to a satisfactory foam cosmetic composition. Aesthetics, product distribution, and/or performance can be affected by the stability of the foam. There is still a need for the development of a foam cosmetic composition that includes large amounts of heavy silicones or oils and can still form a fine and/or stable foam. As used therein, the term "stable foam" means a foam having a life-span longer than about one minute after being created.

It has now been surprisingly and unexpectedly discovered that a composition including an anionic thickening agent, when neutralized with two different bases, can provide a stable foam despite the inclusion of high levels of silicones and/or oils. Such compositions may be useful in applications wherein benefits such as a stable foam, even product distribution, and/or good product performance is desired.

SUMMARY

The disclosure relates, in various embodiments, to a foaming cosmetic composition comprising: at least one anionic thickening agent; at least two alkaline compounds; and at least one silicone.

In further embodiments, the at least one anionic thickening agent is chosen from anionic polyurethanes, anionic guar gums, anionic acrylates copolymers, or anionic polyacrylates.

According to certain embodiments, the at least two alkaline compounds are chosen from hydroxide-containing compounds chosen from alkali metal hydroxides, alkaline-earth metal hydroxides, transition metal hydroxides such as sodium hydroxide, potassium hydroxide, lithium hydroxide, calcium hydroxide, magnesium hydroxide, barium hydroxide, strontium hydroxide, manganese hydroxide, and zinc hydroxide; ammonia; organic amines such as monoethanolamine, diethanolamine, triethanolamine, N-methylglucamine, aminomethyl propanol, aminomethyl propanediol, ethoxylated amines, PEG-25 cocamine, polyoxyethylene (5) cocamine, polyoxyethylene (25) cocamine, polyoxyethylene (5) octadecylamine, polyoxyethylene (25) octadecylamine, polyoxyethylene (5) tallowamine, polyoxyethylene (15) oleylamine, polyethylene (5) soyamine, and polyoxyethylene (25) soyamine; basic amino acids such as arginine and lysine; and mixtures thereof.

The at least one silicone is chosen from silicones or aminofunctional silicones. In particular, the at least one silicone is chosen from PEG-40/PPG-8 methylaminopropyl/hydroxypropyl dimethicone copolymers, amodimethicone/morpholinomethyl silsesquioxane copolymers, amodimethicones, or mixtures thereof.

Other embodiments of the disclosure include a method of preparing a foaming cosmetic composition, the method comprising:

mixing at least one anionic thickening agent and at least one silicone with at least one solvent to form a first part;

adding a first alkaline compound to the first part and stirring to form a first neutralized composition; and adding a second alkaline compound to the first neutralized composition and stirring to form a foaming cosmetic composition.

Some embodiments of the disclosure include a method of improving the stability of a foamed cosmetic composition, the method comprising:

mixing at least one anionic thickening agent and at least one silicone with at least one solvent to form a first part;

adding a first alkaline compound to the first part and stirring to form a first neutralized composition;

adding a second alkaline compound to the first neutralized composition and stirring to form a foamable cosmetic composition; and incorporating a gas into the foamable cosmetic composition to form a foamed cosmetic composition.

Additional features and advantages of the disclosed embodiments as claimed will be set forth in the detailed description which follows, and in part will be readily apparent to those skilled in the art from that description or recognized by practicing the invention as claimed herein, including the detailed description which follows, as well as the claims.

It is to be understood that both the foregoing general description and the following detailed description present various embodiments of the disclosure, and are intended to provide an overview or framework for understanding the nature and character of the claims.

BRIEF DESCRIPTION OF THE DRAWINGS

The accompanying drawings, which are included to provide a further understanding of the invention and are incor

DETAILED DESCRIPTION

Figure 1A:
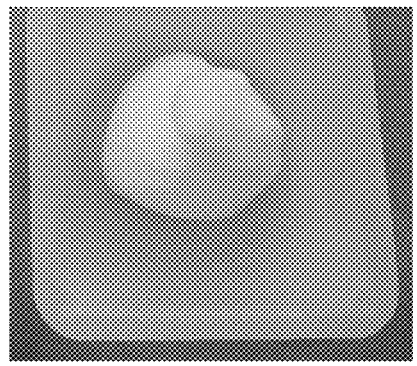
- FIG. 1A is a photograph showing foam according to Example 1 immediately after being dispensed.

In various embodiments, the disclosure relates to a composition in the form of a foam or mousse for caring for, treating, and/or making up keratin materials, for example the skin and/or hair.

The composition according to embodiments of the disclosure may be used as, for example, a composition for treating, making up, or caring for keratinous substances, in particular the hair, skin, lips, eyelashes, eyebrows, or nails. The makeup composition may be selected from, for example, a hair styling product, a hair cleansing product, a hair coloring and/or bleaching product, a cosmetic makeup product for the face, and a product for making up the body or coloring the skin.

Thickening Agent

The compositions according to the disclosed embodiments comprise at least one anionic thickening agent. Thickening agents can also be referred to interchangeably herein as thickeners or rheology modifiers. Thickening agents are generally used to modify the viscosity and/or rheology of the composition. As used herein, the term "thickening agent" means compounds which, by their presence, increase the viscosity of the composition into which they are introduced by at least 20 cps, such as by at least 50 cps, at 25° C. and at a shear rate of 1 s$^{-1}$. The viscosity may be measured using a cone/plate viscometer, a Haake R600 rheometer, or the like.

In certain embodiments, the at least one anionic thickening agent may be chosen from those conventionally used in cosmetics, such as polymers of natural origin and synthetic polymers, and other known rheology modifiers, such as cellulose-based thickeners.

In certain embodiments, the anionic thickening agents may be chosen from hydrophilic thickeners, for example cellulose polymers and gums. As used herein, the term "hydrophilic thickener" is meant to indicate that the thickening agent is soluble or dispersible in water. Non-limiting examples of hydrophilic thickeners include modified or unmodified carboxyvinyl polymers, such as those sold under the tradename Carbopol® (CTFA name: carbomer) by the company Goodrich; homopolymers or copolymers of acrylic or methacrylic acids or the salts thereof and the esters thereof, such as those sold under the tradenames Versicol F® or Versicol K® by the company Allied Colloid, or under the tradename Ultrahold 8® by the company Ciba-Geigy; polyacrylates and polymethacrylates such as copolymers of (meth)acrylic acid, methylacrylate and dimethyl meta-isopropenyl benzyl isocyanate of ethoxylated alcohol (INCI name: Polyacrylate-3) sold under the tradename Viscophobe® DB 1000 from The Dow Chemical Company, those sold under the tradenames Lubrajel and Norgel by the company Guardian, or under the tradename Hispajel by the company Hispano Chimica; and polyacrylic acids of Synthalen® K type, polyacrylamides, copolymers of acrylic acid and of acrylamide sold in the form of the sodium salt thereof, such as those sold under the tradenames Reten® by Hercules, sodium polymethacrylate such as those sold under the tradename Darvan® 7 by the company Vanderbilt, and the sodium salts of polyhydroxycarboxylic acids such as those sold under the tradename Hydagen F® by the company Henkel, optionally crosslinked and/or neutralized 2-acrylamido-2-methylpropanesulphonic acid polymers and copolymers, for instance poly(2-acrylamido-2-methylpropanesulphonic acid) such as those sold under the tradename Hostacerin® AMPS (CTFA name: ammonium polyacryldimethyltauramide) by the company Clariant, crosslinked anionic copolymers of acrylamide and of AMPS, e.g. in the form of a water-in-oil emulsion, such as those sold under the tradename Sepigel™ 305 (CTFA name: Polyacrylamide/C13-14 Isoparaffin/Laureth-7) and under the tradename Simugel™ 600 (CTFA name: Acrylamide/Sodium acryloyldimethyltaurate copolymer/Isohexadecane/Polysorbate 80) by the company Seppic, polyacrylic acid/alkyl acrylate copolymers of Pemulen™ type, associative polymers, for instance PEG-150/stearyl alcohol/SMDI copolymer such those as sold under the tradename ACULYN™ 46 by the company Rohm & Haas, steareth-100/PEG-136/HDI copolymer such as those sold under the tradename Rheolate® FX 1100 by the company Elementis, and mixtures thereof.

In certain embodiments, the hydrophilic thickener may be chosen from anionic associative polymers. As used herein, the term "associative polymer" is intended to mean any polymer comprising in its structure at least one fatty chain and at least one hydrophilic portion.

In certain embodiments, the associative polymers may be chosen from polymers comprising at least one hydrophilic unit and at least one fatty-chain allyl ether unit; polymers in which the hydrophilic unit is constituted of an ethylenic unsaturated anionic monomer, such as a vinylcarboxylic acid, acrylic acid, methacrylic acid, or mixtures thereof; and polymers in which the fatty-chain allyl ether unit corresponds to the monomer of formula (I) below:

$$CH_2=C(R')CH_2OB_nR \qquad (I)$$

in which R' is chosen from H or $CH_3$, B is an ethyleneoxy radical, n is zero or is chosen from an integer ranging from 1 to 100, and R is a hydrocarbon-based radical chosen from alkyl, arylalkyl, aryl, alkylaryl, or cycloalkyl radicals containing from 8 to 30 carbon atoms, from 10 to 24 carbon atoms, or from 12 to 18 carbon atoms. Exemplary and non-limiting polymers of this type are described and prepared, according to an emulsion polymerization process, in patent EP 0 216 479, incorporated by reference herein.

In certain embodiments, the associative anionic polymer may be chosen from anionic polymers comprising at least one hydrophilic unit of olefinic unsaturated carboxylic acid type, and at least one hydrophobic unit exclusively of ($C_{10}$-$C_{30}$)alkyl ester of unsaturated carboxylic acid type.

In certain embodiments, the at least one thickening agent is chosen from copolymers resulting from the polymerization of at least one monomer (a) chosen from carboxylic acids possessing α,β-ethylenically unsaturated groups or their esters, with at least one monomer (b) possessing ethylenically unsaturated groups and comprising a hydrophobic group. Such copolymers may exhibit emulsifying properties.

As used herein, the term "copolymers" is intended to mean both copolymers obtained from two types of monomers and those obtained from more than two types of monomers, such as, for example, terpolymers obtained from three types of monomers. The chemical structure of the copolymers comprises at least one hydrophilic unit and at least one hydrophobic unit. The expression "hydrophobic unit" or "hydrophobic unit" is understood to mean a radical possessing a saturated or unsaturated and linear or branched hydrocarbon-based chain which comprises at least 8 carbon atoms, for example from 10 to 30 carbon atoms, as a further example from 12 to 30 carbon atoms, and as yet a further example from 18 to 30 carbon atoms.

In certain embodiments, the thickening copolymer may be chosen from the copolymers resulting from the polymerization of:

(1) at least one monomer of formula (II):

wherein R1 is chosen from H, $CH_3$, or $C_2H_5$, providing acrylic acid, methacrylic acid, or ethacrylic acid monomers, and (2) at least one monomer of $(C_{15}$-$C_{30})$alkyl ester of unsaturated carboxylic acid type corresponding to the monomer of formula (III):

wherein R2 is chosen from H, $CH_3$, or $C_2H_5$, providing acrylate, methacrylate or ethacrylate units, and R3 denotes a $C_{10}$-$C_{30}$ alkyl radical, such as a $C_{12}$-$C_{22}$ alkyl radical.

In certain embodiments, the $(C_{10}$-$C_{30})$alkyl esters of unsaturated carboxylic acids may be chosen from lauryl acrylate, stearyl acrylate, decyl acrylate, isodecyl acrylate, dodecyl acrylate or the corresponding methacrylates, such as lauryl methacrylate, stearyl methacrylate, decyl methacrylate, isodecyl methacrylate or dodecyl methacrylate, or mixtures thereof.

In certain embodiments, the crosslinked thickening polymer may be chosen from polymers resulting from the polymerization of a mixture of monomers comprising:

(1) acrylic acid, (2) an ester of formula (III) described above, in which R2 is chosen from H or $CH_3$, R3 denotes an alkyl radical having from 12 to 22 carbon atoms, and (3) a crosslinking agent, which is a known copolymerizable polyethylenic unsaturated monomer, such as diallyl phthalate, allyl (meth)acrylate, divinylbenzene, (poly)ethylene glycol dimethacrylate and methylenebisacrylamide.

In various embodiments, the crosslinked thickening polymer may comprise from about 60% to about 95% by weight of acrylic acid (hydrophilic unit), from about 4% to about 40% by weight of $C_{10}$-$C_{30}$ alkyl acrylate (hydrophobic unit), and from about 0% to about 6% by weight of crosslinking polymerizable monomer. In further embodiments, the crosslinked thickening polymer may comprise from about 96% to about 98% by weight of acrylic acid (hydrophilic unit), from about 1% to about 4% by weight of $C_{10}$-$C_{30}$ alkyl acrylate (hydrophobic unit), and from about 0.1% to 0.6% by weight of crosslinking polymerizable monomer, such as those described above.

In certain embodiments, the crosslinked thickening polymer may be chosen from acrylate/$C_{10}$-$C_{30}$ alkyl acrylate copolymers (INCI name: Acrylates/C10-30 Alkyl Acrylate Crosspolymer), such as the products sold under the tradenames Pemulen™ TR1, Pemulen™ TR2, Carbopol® 1382 and Carbopol® EDT 2020 by the company Lubrizol.

In certain embodiments, the anionic thickening agent may be chosen from gellifying agents and/or viscosity modifying agents.

The anionic thickening agent of the present disclosure may also be known as rheology modifiers such as acrylate- or acrylic-based polymers, carbomers, crosslinked homopolymers of acrylic acid or of acrylamidopropane-sulfonic acid, and crosslinked copolymers of (meth)acrylic acid and/or (C1-C6)alkyl esters.

In an embodiment, the anionic thickening agent is chosen from polyacrylate-3, commercially known under the trade name of Viscophobe DB-100 and sold by The Dow Chemical Company, carbomers, commercially known under the trade name of Carbopol polymers and sold by Lubrizol Advance Materials, Inc, acrylates/C10-30 alkyl acrylate crosspolymers, commercially known the trade names of Pemulen TR-1 and Pemulen TR-2 polymers and sold by Lubrizol Advance Materials, Inc, Acrylates/C10-30 Alkyl Acrylate Crosspolymer such as Carbopol® Ultrez 20 Polymer by and sold by Lubrizol Advance Materials, Inc, AMP-acrylates/allyl methacrylate copolymer, commercially known under the trade name of Fixate G-100 polymer and sold by Lubrizol Advance Materials, Inc., Polyacrylate Crosspolymer-6 such as Sepimax™ Zen by the company Seppic, and a crosslinked methacrylic acid/ethyl acrylate copolymer, also known as an acrylates copolymer in aqueous dispersion, such as the slightly cross-linked, alkali-swellable acrylate polymer known by the INCI name acrylates copolymer and sold by Lubrizol, under the tradename CARBOPOL Aqua SF-1 as an aqueous dispersion comprising about 30 percent by weight of total solids or active material.

According to various embodiments, the total amount of anionic thickening agent ranges from about 0.01% to about 15% by weight, from about 0.1% to about 10% by weight, from about 0.2% to about 5% by weight, or from about 0.3% to about 2% by weight, relative to the total weight of the composition.

Neutralizing Base

In certain embodiments, when an anionic thickening agent is used, it is generally neutralized before being included in, or as it is, added to the compositions of the disclosure. Such an anionic thickening agent may be neutralized by employing traditional neutralizing agents, also known as neutralizing bases. As used herein, a "neutralizing base" is an alkaline compound that partially or totally neutralizes the negative charge of the anionic thickener.

According to some embodiments of the disclosure, the composition comprises at least two different alkaline components employed as neutralizing bases.

Nonlimiting examples of neutralizing bases include hydroxide-containing compounds chosen from alkali metal hydroxides, alkaline-earth metal hydroxides, transition metal hydroxides such as sodium hydroxide, potassium hydroxide, lithium hydroxide, calcium hydroxide, magnesium hydroxide, barium hydroxide, strontium hydroxide, manganese hydroxide, and zinc hydroxide; ammonia; organic amines such as monoethanolamine, diethanolamine, triethanolamine, N-methylglucamine, aminomethyl propanol, aminomethyl propanediol, ethoxylated amines, PEG-25 cocamine, polyoxyethylene (5) cocamine, polyoxyethylene (25) cocamine, polyoxyethylene (5) octadecylamine, polyoxyethylene (25) octadecylamine, polyoxyethylene (5) tallowamine, polyoxyethylene (15) oleylamine, polyethylene (5) soyamine, and polyoxyethylene (25) soyamine; basic amino acids such as arginine and lysine; and mixtures thereof.

According to some embodiments, the neutralizing bases are chosen from aminomethyl propanol and triethanolamine.

In certain embodiments, a first neutralizing base and a second neutralizing base are added to the composition at different times. According to some embodiments, a first neutralizing base is added to the composition including an anionic thickener, and a second neutralizing base is added to the composition at a later time. In some embodiments, the first neutralizing base is triethanolamine and the second neutralizing base is aminomethyl propanol.

According to various embodiments of the disclosure, the addition of at least two neutralizing bases will slightly thicken the composition. Without wishing to be bound by theory, in some embodiments a slightly thickened composition may provide a foam having better structure and/or better stability.

In certain embodiments, each of the neutralizing bases is present in an amount ranging from about 0.001% to about 10% by weight, from 0.005% to about 5% by weight, from about 0.01% to about 3% by weight, from about 0.05% to about 2% by weight, from about 0.05% to about 1% by weight, from about 0.05% to about 0.5% by weight, from about 0.1% to about 1.5% by weight, or from about 0.2% to about 1.0% by weight, relative to the weight of the composition.

In certain embodiments, the neutralizing bases are present in a combined amount ranging from 0.001% to about 10% by weight, from 0.005% to about 8% by weight, from about 0.01% to about 6% by weight, from about 0.05% to about 5% by weight, from about 0.1% to about 3% by weight, from about 0.15% to about 1.0% by weight, or from about 0.2% to about 1.0% by weight, relative to the weight of the composition.

In other embodiments, the combined amount of neutralizing bases may be about 0.1%, about 0.15%, about 0.2%, about 0.25%, about 0.3%, about 0.4%, about 0.5%, about 0.6%, about 0.7%, about 0.8%, about 0.9%, about 1.0%, about 2%, about 3%, or about 4% by weight, relative to the weight of the composition.

In certain embodiments, the weight ratio of the at least two neutralizing bases, for example the first neutralizing base to the second neutralizing base, may range from about 10:1 to about 1:10, from about 9:1 to about 1:9, from about 8:1 to about 1:8, from about 7:1 to about 1:7, from about 6:1 to about 1:6, from about 5:1 to about 1:5, from about 4:1 to about 1:4, from about 3:1 to about 1:3, or from about 2:1 to about 1:2.

In other embodiments, the weight ratio of the first neutralizing base to the second neutralizing base is about 10:1, about 9:1, about 8:1, about 7:1, about 6:1, about 5:1, about 4:1, about 3:1, about 2.5:1, about 2:1, about 1:1, about 1:2, about 1:3, about 1:4, about 1:5, about 1:6, about 1:7, about 1:8, about 1:9, or about 1:10.

Silicone

The compositions according to the disclosed embodiments comprise at least one silicone.

In some embodiments, the silicone may comprise silicones, aminofunctional silicones, silicone oils, silicone fluoro oils, or mixtures thereof.

As used herein, the term "silicone oil" means an oil comprising at least one silicon atom, and especially at least one Si—O group. As used herein, the term "oil" means any fatty substance that is in liquid form at room temperature and at atmospheric pressure, for example from about 20° C. to about 25° C. and about 1 atm. The silicone oils may be volatile or non-volatile, and preferably non-volatile oil. As used herein, the term "volatile oil" means any non-aqueous medium that is capable of evaporating on contact with the hair, skin, lips, or nails in less than one hour, at room temperature and atmospheric pressure. In some embodiments, the volatile oil is a cosmetic volatile oil, which is liquid at room temperature. More specifically, a volatile oil has an evaporation rate ranging from about 0.01 mg/cm$^2$/min to about 200 mg/cm$^2$/min.

As used herein, the term "non-volatile oil" means an oil that remains on the hair, skin, lips, or nails at room temperature and atmospheric pressure. According to some embodiments, a non-volatile oil has an evaporation rate of less than about 0.01 mg/cm$^2$/min.

To measure this evaporation rate, 15 g of oil or of oil mixture to be tested is placed in a crystallizing dish 7 cm in diameter, which is placed on a balance in a chamber of about 0.3 m$^3$ that is temperature-controlled, at a temperature of about 25° C., and humidity-controlled, at a relative humidity of about 50%. The liquid is allowed to evaporate freely, without stirring it, while providing ventilation by means of a fan (for example Papst-Motoren, reference 8550 N, rotating at 2700 rpm) placed in a vertical position above the crystallizing dish containing said oil or said mixture, the blades being directed towards the crystallizing dish, about 20 cm away from the bottom of the crystallizing dish. The mass of oil remaining in the crystallizing dish is measured at regular intervals to determine the evaporation rate.

Volatile silicone oils that may also be used include volatile linear or cyclic silicone oils, especially those with a viscosity of less than or equal to 8 centistokes (cSt), and especially containing from 2 to 10 silicon atoms and in particular from 2 to 7 silicon atoms. These silicones optionally comprise alkyl or alkoxy groups containing from 1 to 10 carbon atoms. As volatile silicone oils that may be used in the invention, mention may be made of dimethicones with viscosities of 5 and 6 cSt, octamethylcyclotetrasiloxane, decamethyl-cyclopentasiloxane, dodecamethylcyclohexasiloxane, heptamethylhexyltrisiloxane, heptamethyloctyltrisiloxane, hexamethyldisiloxane, octamethyltrisiloxane, decamethyl-tetrasiloxane and dodecamethylpentasiloxane, and mixtures thereof.

In one embodiment, a composition comprises from less than about 15.0%, such as from about 0% to about 10.0%, or from about 0 to about 5.0% by weight of volatile silicone oil relative to the total weight of the foam cosmetic composition.

According to some embodiments, the non-volatile silicone oil may be chosen from:

oils of high molar mass, in particular having a molar mass ranging from about 400 g/mol to about 10,000 g/mol, in particular from about 650 g/mol to about 10,000 g/mol, in particular from about 750 g/mol to about 7,500 g/mol and more particularly ranging from about 1,000 g/mol to about 5,000 g/mol;

optionally partially silicone fluoro oils, for example fluorosilicone oils and fluorosilicones as described in document EP-A-847 752, incorporated by reference herein;

silicone oils, for example linear or cyclic non-volatile polydimethylsiloxanes (PDMS);

polydimethylsiloxanes comprising alkyl, alkoxy or phenyl groups, which are pendent or at the end of a silicone chain, these groups containing from 2 to 24 carbon atoms;

phenyl silicones, for example phenyl trimethicones, phenyl dimethicones, phenyl trimethylsiloxy diphenyl siloxanes, diphenyl dimethicones, diphenyl methyldiphenyl trisiloxanes and 2-phenylethyl trimethylsiloxy silicates; and mixtures thereof.

In certain embodiments, the composition comprises at least one aminofunctional silicone.

In certain embodiments, the aminofunctional silicone may be chosen from those having morpholino groups, corresponding to the compounds of formula (V) below:

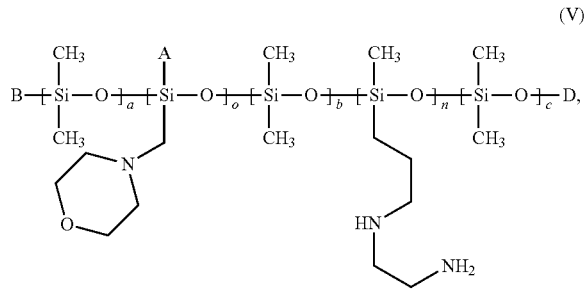

(V)

wherein

A represents —OH, or a structural unit (I), (II), or (III) bound via —O—

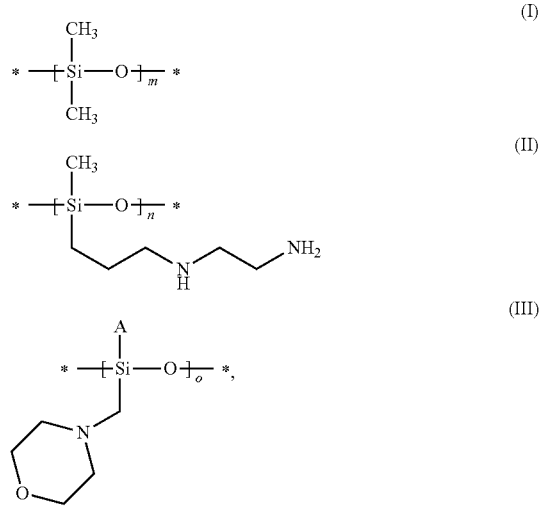

or an oligomeric or polymeric residue, bound via —O—, containing structural units of formulas (I), (II), or (III), or half of a connecting oxygen atom to a structural unit (III),

* represents a bond to one of the structural units (I), (II), or (III), or denotes a terminal group B (Si-bound) or D (O-bound), B is chosen from an —OH, —O—Si(CH$_3$)$_3$, —O—Si(CH$_3$)$_2$OH, or —O—Si(CH$_3$)$_2$OCH$_3$ group, D is chosen from an —H, —Si(CH$_3$)$_3$, —Si(CH$_3$)$_2$OH, or —Si(CH$_3$)$_2$OCH$_3$ group, a, b, and c independently represent integers ranging from 0 to 1000, with the provision that a+b+c>0, m, n, and o independently represent integers ranging from 1 to 1000.

Aminofunctional silicones of this kind bear the INCI name Amodimethicone/Morpholinomethyl Silsesquioxane Copolymer, for example those sold under the tradename Belsil® ADM 6300 E by the company Wacker.

In certain embodiments, the aminofunctional silicone may be chosen from those corresponding to formula (Si-2) below:

$$M(R_aQ_bSiO_{(4-a-b)/2})_x(R_cSiO_{(4-c)/2})_yM \qquad (Si\text{-}2);$$

wherein,

R is a hydrocarbon or a hydrocarbon residue having 1 to approximately 6 carbon atoms;

Q is a polar residue of the general formula —R$^1$HZ, wherein

R$^1$ is a divalent connecting group that is bound to the hydrogen and to the Z residue, assembled from carbon and hydrogen atoms; carbon, hydrogen, and oxygen atoms; or carbon, hydrogen, and nitrogen atoms, and Z is an organic aminofunctional residue that contains at least one aminofunctional group;

a is a number ranging from about 0 to about 2, b is a number ranging from about 1 to about 3, with the proviso that a+b is less than or equal to 3;

c is a number ranging from about 1 to about 3;

x is a number ranging from about 1 to about 2,000, from about 3 to about 50, or from about 3 to about 25;

y is a number ranging from about 20 to 10,000, from about 125 to about 10,000, or from about 150 to about 1,000; and M is a suitable silicone terminal group known in the existing art, such as trimethylsiloxy.

In other embodiments, Z according to formula (Si-2) may be an organic aminofunctional residue containing at least one functional amino group. In other embodiments, Z may correspond to the formula —NH(CH$_2$)$_z$NH$_2$, wherein z is an integer greater than or equal to 1. In other embodiments, Z may correspond to the formula —NH(CH$_2$)$_z$(CH$_2$)$_{zz}$NH, wherein both z and zz, independently of each other, are an integer greater than or equal to 1, and the said structure encompasses diamino ring structures such as piperazinyl. In other embodiments, Z may correspond to the formula —NHCH$_2$CH$_2$NH$_2$. In other embodiments, Z may correspond to the formula —N(CH$_2$)$_z$(CH$_2$)$_{zz}$NX$_2$ or —NX$_2$, wherein each X$_2$ is selected independently from the group consisting of hydrogen and alkyl groups having 1 to 12 carbon atoms, and zz is equal to 0.

In certain embodiments, Q according to formula (Si-2) may be a polar aminofunctional residue corresponding to the formula —CH$_2$CH$_2$CH$_2$NHCH$_2$CH$_2$NH$_2$.

Such silicones are sold under the tradenames Dow Corning (DC) 929 Emulsion, DC2-2078, and DC5-7113, by the company Dow Corning, SM2059 by the company General Electric, and SLM-55067 by the company Wacker.

In certain embodiments, the aminofunctional silicone may be chosen from those cationic aminofunctional silicone polymers corresponding to formula (Si3-a) below:

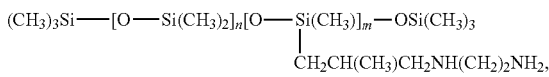

(Si-3a)

where m and n are numbers whose sum (m+n) ranges from 1 to 2000 or from 50 to 150, where n is a number chosen from 0 to 1999 or from 49 to 149, and m is a number chosen from 1 to 2000 or from 1 to 10.

These silicones are referred to by the INCI name trimethylsilylamodimethicones and are available, for example, under the tradename Q2-7224 by the company Dow Corning.

In certain embodiments, the aminofunctional silicone may be chosen from those corresponding to formula (Si-3b) below:

(Si-3b)

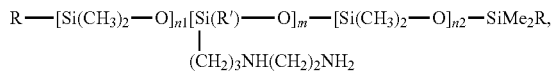

$$\underset{(CH_2)_3NH(CH_2)_2NH_2}{R\text{—}[Si(CH_3)_2\text{—}O]_{n1}[Si(R')\text{—}O]_m\text{—}[Si(CH_3)_2\text{—}O]_{n2}\text{—}SiMe_2R,}$$

wherein

Me denotes a methyl group,

R may be the same or different, and at least one R is chosen from —OH, a ($C_1$ to $C_{20}$) alkyl group, an ethoxylated and/or propoxylated ($C_1$ to $C_{20}$) alkoxy group, a methoxy group, an ethoxy group, or a —$CH_3$ group, R' is chosen from an —OH, a ($C_1$ to $C_{20}$) alkoxy group, or a —$CH_3$ group, and m, n1, and n2 are numbers whose sum (m+n1+n2) ranges from 1 to 2000 or from 50 to 150, wherein the sum (n1+n2) ranges from 0 to 1999 or from 49 to 149, and m is a number ranging from 1 to 2000 or from 1 to 10.

These silicones are referred to by the INCI name Amodimethicones or as functionalized Amodimethicones, for example Bis(C13-15 Alkoxy) PG Amodimethicone, sold under the tradename DC 8500 by the company Dow Corning, Trideceth-9 PG-Amodimethicone, sold under the tradename Silcare® Silicone SEA by the company Clariant, Amodimethicone (and) Trideceth-10 sold under the tradename Belsil® ADM 6102 E by the company Wacker, and those sold under the tradenames Wacker Belsil® ADM 652, Wacker Belsil® ADM 653, or Wacker Belsil® ADM 8020 by the company Wacker.

In other embodiments, the aminofunctional silicone may be chosen from polyammonium-polysiloxane compounds, which may be available under the tradename Baysilone®, including Baysilone® TP 3911, SME 253 and SFE 839, by the company GE Bayer Silicones. Polyammonium-polysiloxane compounds can be acquired, for example, from GE Bayer Silicones under the tradename Baysilone®.

According to certain embodiments of the disclosure, the aminofunctional silicone is chosen from those under the INCI name PEG-40/PPG-8 methylaminopropyl/hydroxypropyl dimethicone copolymer sold under the tradename Silsoft® A+ from Momentive, those under the INCI name amodimethicone/morpholinomethyl silsesquioxane copolymer sold under the tradename Belsil® ADM 8301 E from Wacker, an emulsion of amodimethicone/morpholinomethyl silsesquioxane copolymer (and) amodimethicone (and) trideceth-10 (and) acetic acid sold under the tradename Belsil® ADM 6300 E from Wacker, those under the INCI name amodimethicone, or mixtures thereof.

In some embodiments, the at least one aminofunctional silicone chosen from amodimethicone is provided as an emulsion that further comprises surfactants chosen from nonionic or cationic surfactants, or mixtures thereof. Examples of such nonionic surfactants include ethoxylated tridecanol (INCI name: Trideceth-5) and α-isotridecyl-ω-hydroxy polyglycol ether (INCI name: Trideceth-10). An example of the cationic surfactant that may be present in the emulsion is cetrimonium chloride. In certain other embodiments, the compositions of the disclosure comprise at least one aminofunctional silicone chosen from amodimethicone which is provided as an emulsion that further comprises nonionic surfactants chosen from trideceth-5, trideceth-10, or mixtures thereof.

In various embodiments, the at least one aminofunctional silicone may be present in an amount ranging from about 0.01% to about 10% by weight, from about 0.05% to about 7.5% weight, from about 0.1% to about 5% weight, and from about 0.5% to about 2.5% by weight, relative to the total weight of the composition.

In certain embodiments, a composition may comprise from about 0.01% to about 50.0%, such as from about 0.1% to about 30.0%, from about 0.2% to about 20.0%, from about 0.5% to about 15.0%, from about 1.0% to about 10.0%, from about 1.5% to about 7.5%, from about 2.0% to about 5.0% by weight of non-volatile oil, relative to the total weight of foam cosmetic composition.

According to certain embodiments, the silicone may be present in an amount ranging from about 0.1% to about 50%, from about 0.2% to about 40%, from about 0.3% to about 30%, from about 0.5% to about 20%, from about 0.6% to about 10%, or from about 0.65% to about 5%.

Surfactant

The compositions according to the disclosed embodiments comprise at least one surfactant.

In particular, the surfactant is chosen from anionic, amphoteric, zwitterionic, cationic, and nonionic surfactants.

The term "anionic surfactant" means a surfactant comprising, as ionic or ionizable groups, only anionic groups. Nonlimiting examples of these anionic groups include the groups —C(O)OH, —C(O)O—, —$SO_3H$, —$S(O)_2O$—, —$OS(O)_2OH$, —$OS(O)_2O$—, —$P(O)OH_2$, —$P(O)_2O$—, —$P(O)O_2$—, —$P(OH)_2$, =$P(O)OH$, —$P(OH)O$—, =$P(O)O$—, =POH and =PO—, the anionic parts comprising a cationic counterion such as an alkali metal, an alkaline-earth metal or an ammonium.

As examples of anionic surfactants that may be used in the dye composition according to the invention, mention may be made of alkyl sulfates, alkyl ether sulfates, alkylamido ether sulfates, alkylarylpolyether sulfates, monoglyceride sulfates, alkylsulfonates, alkylamidesulfonates, alkylarylsulfonates, α-olefin sulfonates, paraffin sulfonates, alkylsulfosuccinates, alkylether sulfosuccinates, alkylamide sulfosuccinates, alkylsulfoacetates, acylsarcosinates, acylglutamates, alkylsulfosuccinamates, acylisethionates and N-acyltaurates, salts of alkyl monoesters of polyglycoside-polycarboxylic acids, acyllactylates, D-galactoside uronic acid salts, alkyl ether carboxylic acid salts, alkylaryl ether carboxylic acid salts, alkylamido ether carboxylic acid salts, and the corresponding non-salified forms of all these compounds, the alkyl and acyl groups of all these compounds comprising from 6 to 40 carbon atoms and the aryl group denoting a phenyl group.

These compounds can be oxyethylenated and then preferably comprise from 1 to 50 ethylene oxide units.

The salts of $C_6$-$C_{24}$ alkyl monoesters of polyglycoside-polycarboxylic acids can be chosen from $C_6$-$C_{24}$ alkyl polyglycoside-citrates, $C_6$-$C_{24}$ alkyl polyglycoside-tartrates and $C_6$-$C_{24}$ alkyl polyglycoside-sulfosuccinates.

When the anionic surfactant is in salt form, it may be chosen from alkali metal salts such as sodium or potassium salt and preferably sodium salt, ammonium salts, amine salts and in particular amino alcohol salts or alkaline-earth metal salts such as magnesium salts.

Examples of amino alcohol salts that may especially be mentioned include monoethanolamine, diethanolamine and triethanolamine salts, monoisopropanolamine, diisopropanolamine or triisopropanolamine salts, 2-amino-2-methyl-1-propanol salts, 2-amino-2-methyl-1,3-propanediol salts and tris(hydroxymethyl)aminomethane salts.

According to some embodiments, alkali metal or alkaline-earth metal salts, and in particular sodium or magnesium salts, are used.

In other embodiments, the anionic surfactant is chosen from $(C_6$-$C_{24})$alkyl sulfates, $(C_6$-$C_{24})$alkyl ether sulfates comprising from 2 to 50 ethylene oxide units, in particular in the form of alkali metal, ammonium, amino alcohol and alkaline-earth metal salts, $(C_{12}$-$C_{20})$alkyl sulfates, $(C_{12}$-$C_{20})$alkyl ether sulfates comprising from 2 to 20 ethylene oxide units, in particular in the form of alkali metal, ammonium, amino alcohol and alkaline-earth metal salts, sodium lauryl ether sulfate containing 2.2 mol of ethylene oxide, or mixtures thereof.

The amphoteric or zwitterionic surfactant may be derivatives of optionally quaternized secondary or tertiary aliphatic amines, in which derivatives the aliphatic group is a linear or branched chain comprising from 8 to 22 carbon atoms, the said amine derivatives comprising at least one anionic group, such as, for example, a carboxylate, sulfonate, sulfate, phosphate or phosphonate group. Mention may be made in particular of $(C_8$-$C_{20})$alkylbetaines, sulfobetaines, $(C_8$-$C_{20})$alkylamido$(C_3$-$C_8)$alkylbetaines and $(C_8$-$C_{20})$alkylamido$(C_6$-$C_8)$alkylsulfobetaines.

Other amphoteric or zwitterionic surfactants include those under the INCI name amphodiacetates, such as disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, disodium capryloamphodipropionate, lauroamphodipropionic acid, cocoamphodipropionic acid, and sodium diethylaminopropyl cocoaspartamide.

According to various embodiments, the amphoteric or zwitterionic surfactant is chosen from $(C_8$-$C_{20})$alkylbetaines such as cocoylbetaine, $(C_8$-$C_{20})$alkylamido$(C_3$-$C_8)$alkylbetaines such as cocoylamidopropylbetaine, the sodium salt of diethylaminopropyl laurylaminosuccinamate (INCI name: sodium diethylaminopropyl cocoaspartamide), {[3-(dodecanoylamino)propyl](dimethyl)ammonio}acetate (INCI name: cocamidopropylbetaine), cocoylbetaine and the sodium salt of diethylaminopropyl laurylaminosuccinamate, and mixtures thereof.

In some embodiments, the cationic surfactant is chosen from salts of optionally polyoxyalkylenated primary, secondary or tertiary fatty amines, quaternary ammonium salts, and mixtures thereof. Nonlimiting examples of cationic surfactants include cetyltrimethylammonium, behenyltrimethylammonium and dipalmitoylethyl-hydroxyethylmethylammonium salts, and mixtures thereof, and more particularly behenyltrimethylammonium chloride, cetyltrimethylammonium chloride, and dipalmitoylethylhydroxyethylammonium methosulfate, and mixtures thereof.

According to certain embodiments, the nonionic surfactant is chosen from alcohols, α-diols and $(C_1$-$C_{20})$alkylphenols, these compounds being etherified with ethoxylated, propoxylated and/or glycerolated groups, and containing at least one fatty chain comprising, for example, from 8 to 18 carbon atoms, it being possible for the number of ethylene oxide and/or propylene oxide groups to range especially from 1 to 100, more particularly from 2 to 50 and even more particularly from 2 to 30, and for the number of glycerol groups to range especially from 1 to 30.

Mention may also be made of copolymers of ethylene oxide and propylene oxide, optionally oxyethylenated fatty acid esters of sorbitan, fatty acid esters of sucrose, oxyalkylenated fatty acid esters, optionally oxyalkylenated alkyl polyglycosides, alkyl glucoside esters, derivatives of N-alkyl glucamine and of N-acyl methylglucamine, aldobionamides and amine oxides.

In some embodiments, the nonionic surfactant is chosen from oxyalkylenated or glycerolated nonionic surfactants. The oxyalkylene units are more particularly oxyethylene or oxypropylene units, or a combination thereof, preferably oxyethylene units.

Nonlimiting examples of the nonionic surfactant include: oxyalkylenated $(C_8$-$C_{24})$alkylphenols; saturated or unsaturated, linear or branched, oxyalkylenated or glycerolated $C_8$-$C_{30}$ alcohols; saturated or unsaturated, linear or branched, oxyalkylenated $C_8$-$C_{30}$ amides; esters of saturated or unsaturated, linear or branched, $C_8$-$C_{30}$ acids and of polyethylene glycols; oxyethylenated esters of saturated or unsaturated, linear or branched $C_8$-$C_{30}$ acids and of sorbitol; saturated or unsaturated oxyethylenated vegetable oils; condensates of ethylene oxide and/or of propylene oxide, either alone or as mixtures; oxyethylenated and/or oxypropylenated silicones; polysorbate-type nonionic surfactants formed by the ethoxylation of sorbitan before the addition of a fatty acid, such as polysorbate 20; and alkyl glucosides such as decyl glucoside.

In some embodiments, the nonionic surfactant contains a number of moles of ethylene oxide and/or of propylene oxide ranging from about 1 to about 100, such as from about 2 to about 50 or from about 2 to about 30. In certain embodiments, the nonionic surfactants do not comprise any oxypropylene units.

According to certain embodiment of the disclosure, the oxyalkylenated nonionic surfactant is chosen from oxyethylenated $C_8$-$C_{30}$ alcohols comprising from 1 to 100 mol of ethylene oxide, preferably from 2 to 50 and more particularly from 2 to 30 mol of ethylene oxide; oxyethylenated esters of linear or branched, saturated or unsaturated $C_8$-$C_{30}$ acids and of sorbitol comprising from 1 to 100 mol of ethylene oxide. As examples of glycerolated nonionic surfactants include glycerolated $C_8$-$C_{40}$ alcohols.

Examples of compounds of this type that may be mentioned include lauryl alcohol containing 4 mol of glycerol (INCI name: Polyglyceryl-4 Lauryl Ether), lauryl alcohol containing 1.5 mol of glycerol, oleyl alcohol containing 4 mol of glycerol (INCI name: Polyglyceryl-4 Oleyl Ether), oleyl alcohol containing 2 mol of glycerol (INCI name: Polyglyceryl-2 Oleyl Ether), cetearyl alcohol containing 2 mol of glycerol, cetearyl alcohol containing 6 mol of glycerol, oleocetyl alcohol containing 6 mol of glycerol, and octadecanol containing 6 mol of glycerol.

Among the glycerolated alcohols, it is more particularly preferred to use the $C_8/C_{10}$ alcohol containing 1 mol of glycerol, the $C_{10}/C_{12}$ alcohol containing 1 mol of glycerol and the $C_{12}$ alcohol containing 1.5 mol of glycerol.

In various embodiments, the amount of surfactant ranges from about 0.0.05% to about 50% by weight, such as from about 0.1% to about 10%, from about 0.2% to about 8%, or from about 0.5% to about 5% by weight, relative to the total weight of the composition.

Polymer

The compositions according to the disclosed embodiments optionally comprise at least one latex polymer or at least one film-forming polymer. In some embodiments, the at least one latex polymer is a film-forming polymer.

As used herein, a "film-forming polymer" is meant to include a polymer that is capable, by itself or in the presence of an auxiliary film-forming agent, of forming a macroscopically continuous film that adheres to keratin materials, and preferably a cohesive film, better still, a film whose cohesion and mechanical properties are such that said film can be isolated and manipulated individually, for example, when said film is prepared by pouring onto a non-stick surface such as Teflon-coated or silicone-coated surface. In addition, as used herein, a non-film-forming polymer is meant to include a polymer which will not form a film at ambient temperature or below, or in other words, will only form a film at temperatures above ambient. For purposes of this disclosure, ambient temperature is taken as being below about 40° C., such as in the range of about 15° C. to about 30° C.

In various embodiments, the polymer is provided in the form of aqueous dispersions prior to formulating the compositions of the disclosure. In other embodiments, the aqueous dispersions may be obtained through an emulsion polymerization of monomers wherein the resulting latex polymer has a particle size less than about 1 µm. In certain other embodiments, a dispersion prepared by the polymerization in water of one or more monomers having a polymerizable double bond may be chosen. In other embodiments, the polymer is produced from condensation reactions between monomers and subsequently dispersed in an aqueous medium.

In various embodiments, the latex polymer may exist as dispersed polymer particles in a dispersion medium, such as an aqueous dispersion medium.

The dispersion medium comprises at least one solvent chosen from water. The dispersion medium may further comprise at least one solvent chosen from cosmetically acceptable organic solvents. Cosmetically acceptable organic solvents may, in various embodiments, be water-miscible, e.g. capable of forming at about 25° C. a homogeneous mixture that is transparent, or substantially transparent, to the eye. For instance, cosmetically acceptable organic solvents may be chosen from lower monoalcohols, such as those containing from about 1 to 5 carbon atoms, for example ethanol and isopropanol; polyols, including glycols, such as those containing from about 2 to 8 carbon atoms, for example propylene glycol, ethylene glycol, 1,3-butylene glycol, dipropylene glycol, hexylene glycol, and glycerin; hydrocarbons, such as, for example, isododecane and mineral oil; and silicones, such as dimethicones, cyclic dimethicones (INCI name: cyclomethicones), and cyclopentasiloxane; or mixtures thereof.

In other embodiments, the solvent of the dispersion medium comprises water. In other embodiments, the solvent of the dispersion medium comprises water and at least one cosmetically acceptable organic solvent. In further embodiments, the solvent comprises water. In further embodiments, the solvent of the dispersion medium primarily consists essentially of water. For example, the solvent of the dispersion medium may, in at least certain exemplary embodiments, comprise greater than about 50% water, greater than about 55% water, greater than about 60% water, greater than about 65% water, greater than about 70% water, greater than about 75% water, greater than about 80% water, greater than about 85% water, greater than about 90% water, greater than about 95% water, greater than about 96% water, greater than about 97% water, greater than about 98% water, or greater than about 99% water.

In various embodiments, the latex polymer particles are not soluble in the solvent of the dispersion medium, i.e. are not water soluble and/or are not soluble in the at least one cosmetically acceptable organic solvent. Accordingly, the latex polymers retain their particulate form in the solvent or solvents chosen.

In another embodiment, the aqueous dispersions obtained through an emulsion polymerization may be spray-dried.

In certain embodiments, latex particles according to the disclosure may have an average diameter ranging up to about 1000 nm, from about 50 nm to about 800 nm, or from about 100 nm to about 500 nm. Such particle sizes may be measured with a laser granulometer (e.g. Brookhaven B190).

In various embodiments, the latex polymer may, independently, be neutralized, partially neutralized, or unneutralized. In other embodiments where the latex polymer is neutralized or partially neutralized, the particle size may be, for example, greater than about 800 nm. In certain embodiments, the particulate form of the latex polymers is retained in the dispersion medium.

In various embodiments, the latex polymer may be chosen from uncharged and charged latex polymers. In other embodiments, the latex polymer may be chosen from non-ionic latex polymers, cationic latex polymers, and anionic latex polymers.

In some embodiments, the latex polymer may be chosen from acrylate latex polymers and polyurethane latex polymers.

In certain embodiments, the latex polymer may be chosen from polyacrylic latex, polyacrylate latex, polystyrene latex, polyester latex, polyamide latex, polyurea latex, polyurethane latex, epoxy resin latex, cellulose-acrylate latex, or their copolymers.

In various embodiments according to the disclosure, polymer may be chosen from non-latex film forming polymers.

In certain embodiments, the total amount of polymer ranges from about 0.001% to about 15% by weight, from 0.05% to about 10% by weight, from about 0.1% to about 7.5% by weight, from about 0.25% to about 5% by weight, from about 0.5% to about 2.5% by weight, or from about 0.5% to about 1.5% by weight, relative to the weight of the composition.

Solvent

The compositions according to the disclosed embodiments comprise a solvent comprising water. The solvent may further comprise at least one cosmetically acceptable organic solvent. Cosmetically acceptable organic solvents may, in various embodiments, be water-miscible, e.g. capable of forming at about 25° C. a homogeneous mixture that is transparent, or substantially transparent, to the eye. In some embodiments, the cosmetically acceptable organic solvent may be chosen from lower monoalcohols, such as those containing from about 1 to 5 carbon atoms, for example ethanol and isopropanol; polyols, including glycols, such as those containing from about 2 to 8 carbon atoms, for example propylene glycol, ethylene glycol, 1,3-butylene glycol, pentylene glycol, hexylene glycol, dipropylene glycol, diethylene glycol, glycerin, ethylhexyl glycerin, glycol ethers especially containing from 3 to 16 carbon atoms such as mono-, di- or tripropylene glycol $(C_1$-$C_4)$alkyl ethers, mono-, di- or triethylene glycol $(C_1$-$C_4)$alkyl ethers, and mixtures thereof.

According to certain embodiments, the solvent may be present in an amount ranging from about 1% to about 99%, from about 5% to about 98%, from about 10% to about 97%, from about 20% to about 96%, from about 30% to about 95%, from about 40% to about 94%, from about 50% to about 93%, from about 60% to about 92%, from about 70% to about 91%, or from about 80% to about 90%.

Propellant

The compositions according to the disclosed embodiments comprise at least one propellant. As used herein, the term "propellant" is meant to indicate a liquid or gas that is packaged with the composition in a device under pressure, which serves to dispense the composition from the device with force and/or facilitate or enhance the foaming of the composition.

Nonlimiting examples of propellants that are suitable for use include gases usually used in the cosmetic field, in particular optionally halogenated volatile hydrocarbons, for example n-butane, propane, isobutane, or pentane, and halogenated derivatives thereof; carbon dioxide, nitrous oxide, dimethyl ether, hydrofluorocarbons, and nitrogen, alone or as mixtures.

In certain embodiments of the disclosure, the propellant is chosen from alkanes and in particular from n-butane, propane, and isobutane, and mixtures thereof.

According to various embodiments, the propellant is under pressure, and at least partially in liquid form.

In certain embodiments, the total amount of propellant ranges from about 1% to about 30% by weight, relative to the weight of the composition, such as from about 2% to about 15% by weight relative to the weight of the composition.

Additional Components

The compositions according to some embodiments of the disclosure may further comprise additional components that are typically used in hair styling compositions. Such components are known to those of skill in the art, or are within the ability of those of skill in the art to determine depending on the particular application, such as, for example, oils, carbonate compounds, emulsifying agents, fillers, pigments, conditioning agents, moisturizing agents, additional viscosity or thickening agents, shine agents, sequestering agents, fragrances, preservatives, pH modifiers, acidic neutralizing agents, stabilizers, or mixtures thereof.

In various embodiments, the composition described herein may have a pH ranging from about 3 to about 9, such as about 4 to about 8, or about 5 to about 7.

In certain exemplary embodiments, the compositions are in the form of hair styling compositions. In various embodiments, the composition may be provided in the form of a foam or a mousse.

In various embodiments, the composition is a hair styling composition. According to various embodiments, by "hair styling composition" the composition is meant to be applied to hair on the head other than eyelashes and/or eyebrows. Hair styling compositions and mascaras are sometimes distinguishable based on the components of the compositions and/or the effects of the compositions when applied. In some embodiments, at least one component of a hair styling composition is not compatible for use in a mascara. In other embodiments, at least one component of a mascara is not compatible for use in a hair styling composition.

According to some embodiments, the composition is not applied to the eyelashes and/or eyebrows. In certain embodiments, the composition is not a mascara.

In certain embodiments, the composition may be applied to the hair by first applying to the hands, and then contacting the hair with the hands. In other embodiments, the composition may be applied directly onto the hair, such as by spraying. The compositions may, in various embodiments, be applied to the hair as a leave-on treatment.

As described, compositions according to the disclosure may produce a foam that has a satisfactory structure and/or stability.

The viscosity of the foam is an indicator of the stability of the foam. In certain embodiments, the viscosity of the foam at room temperature ranges from about 2,000 to about 40,000 centipoise ("cp"), such as from about 15,000 to about 30,000 cp.

Another indication of foam stability is the change in foam structure over time. According to various embodiments, the structure of the foam remains substantially unchanged for at least about 60 minutes, at least about 30 minutes, at least about 15 minutes, at least about 10 minutes, at least about 8 minutes, at least about 6 minutes, at least about 5 minutes, at least about 4 minutes, at least about 3 minutes, at least about 2 minutes, or at least about 1 minute.

It to be understood that, as used herein the terms "the," "a," or "an," mean "at least one," and should not be limited to "only one" unless explicitly indicated to the contrary. Thus, for example, reference to "a portion" includes examples having two or more such portions unless the context clearly indicates otherwise.

It should be understood that all patents and published patent applications referenced are incorporated herein in their entireties.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that any particular order be inferred.

While various features, elements or steps of particular embodiments may be disclosed using the transitional phrase "comprising," it is to be understood that alternative embodiments, including those that may be described using the transitional phrases "consisting" or "consisting essentially of," are implied. Thus, for example, implied alternative embodiments to a method that comprises A+B+C include embodiments where a method consists of A+B+C and embodiments where a method consists essentially of A+B+C. As described, the phrase "at least one of A, B, and C" is intended to include "at least one A or at least one B or at least one C," and is also intended to include "at least one A and at least one B and at least one C."

All ranges and amounts given herein are intended to include subranges and amounts using any disclosed point as an end point. Thus, a range of "1% to 10%, such as 2% to 8%, such as 3% to 5%," is intended to encompass ranges of "1% to 8%," "1% to 5%," "2% to 10%," and so on.

All numbers, amounts, ranges, etc., are intended to be modified by the term "about," whether or not so expressly stated. Similarly, a range given of "about 1% to 10%" is intended to have the term "about" modifying both the 1% and the 10% endpoints.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present disclosure. For example, the term "about" can mean within 10% of the indicated number (e.g. "about 10%" means 9%-11% and "about 2%" means 1.8%-2.2%), such as within 9%, 8%, 7%, 6%, 5%, 4%, 3%, 2%, or 1%, according to various embodiments.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements. The example that follows serves to illustrate embodiments of the present disclosure without, however, being limiting in nature.

It is understood that when an amount of a component is given, it is intended to signify the amount of the active material, unless otherwise indicated.

The compositions and methods according to the present disclosure can comprise, consist of, or consist essentially of the elements and limitations described herein, as well as any additional or optional ingredients, components, or limitations described herein or otherwise known in the art.

It will be apparent to those skilled in the art that various modifications and variations can be made in the delivery system, composition and methods of the invention without departing from the spirit or scope of the invention. Thus, it is intended that the present invention cover the modifications and variations of this invention provided that they come within the scope of the appended claims and their equivalents.

EXAMPLES

The following Examples are provided for illustrative purposes only, and are not intended to be limiting.

In each of the following examples, unless otherwise described or stated, the amounts of components given are in terms of percentage of active material (AM).

Compositions according to Examples 1 and 2, and Comparative Example 1 were prepared by first preparing Part A according to Table 1 below and stirring. Part B including triethanolamine was added to Part A and stirred. Part C including aminomethyl propanol was subsequently added to Examples 1 and 2. The resulting compositions were packaged in respective aerosol devices and charged with the propellant including isobutane and propane.

TABLE 1

| INGREDIENT | Example 1 | Example 2 | Comparative Example 1 |
|---|---|---|---|
| PART A | | | |
| HYDROXYPROPYL GUAR | 0.094 | 0.094 | 0.094 |
| POLYACRYLATE-3 | 0.43 | 0.43 | 0.43 |
| AMODIMETHICONE/ MORPHOLINOMETHYL SILSESQUIOXANE COPOLYMER | 0.26 | 0.26 | 0.26 |
| AMODIMETHICONE | 0.395 | 0.395 | 0.395 |
| LATEX POLYMER | 0.928 | 1.88 | 0.928 |
| NONIONIC SURFACTANTS OF THE POLYSORBATE-TYPE (and) ETHOXYLATED ALCOHOL TYPE (and) AMPHOTERIC SURFACTANTS (and) ALKYLPOLYGLUCOSIDES | 0.486 | 0.486 | 0.486 |
| PROPYLENE GLYCOL (and) ETHYLHEXYLGLYCERIN | 1.0251 | 1.0251 | 1.025 |
| ADDITIONAL COMPONENTS (FRAGRANCE (and) PRESERVATIVE (and) SODIUM LAURYL SULFATE (and) SODIUM CHLORIDE (and) ACETIC ACID) | 1.384 | 1.404 | 1.384 |
| WATER | QS 100 | QS 100 | QS 100 |

TABLE 1-continued

| INGREDIENT | Example 1 | Example 2 | Comparative Example 1 |
|---|---|---|---|
| PART B | | | |
| TRIETHANOLAMINE | 0.141 | 0.141 | 0.141 |
| PART C | | | |
| AMINOMETHYL PROPANOL | 0.0564 | 0.094 | — |
| PROPELLANT | | | |
| ISOBUTANE (and) PROPANE | 6 | 6 | 6 |

The foams resulting from Examples 1 and 2 each had good structure and stability. In particular, the resulting foams were creamy and exhibited a satisfactory and lasting foam viscosity.

As shown in FIG. 1A, the foam resulting from Example 1 was creamy with a good structure immediately after being dispensed. As shown in FIGS. 2A-4A, the foam remained creamy and maintained a good structure and lasting foam viscosity 30 seconds, one minute, and two minutes after being dispensed. The dollop foam of Example 1 exhibited minimal change over two minutes.

Figure 1B:
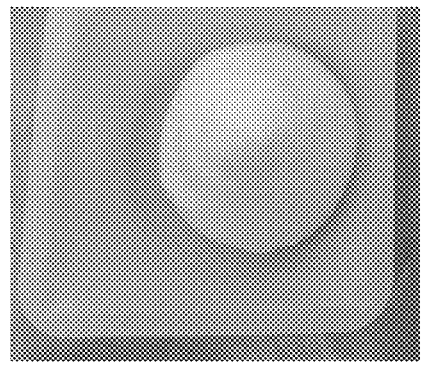
FIG. 1B is a photograph showing foam according to Comparative Example 1 immediately after being dispensed.
Figure 2A:
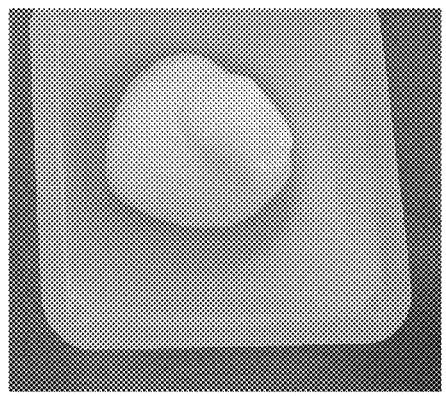
FIG. 2A is a photograph showing foam according to Example 1 30 seconds after being dispensed.
Figure 2B:
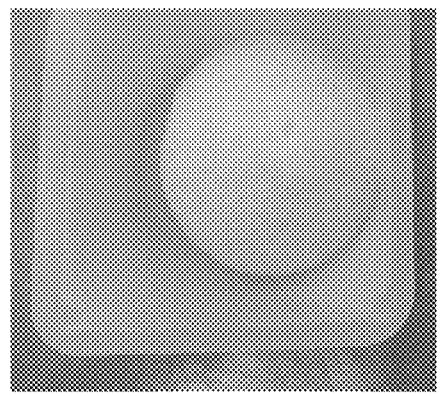
FIG. 2B is a photograph showing foam according to Comparative Example 1 30 seconds after being dispensed.
Figure 3A:
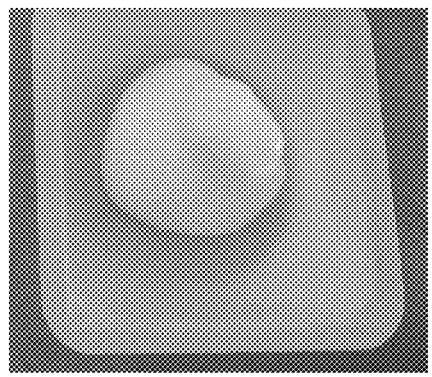
FIG. 3A is a photograph showing foam according to Example 1 one minute after being dispensed.
Figure 3B:
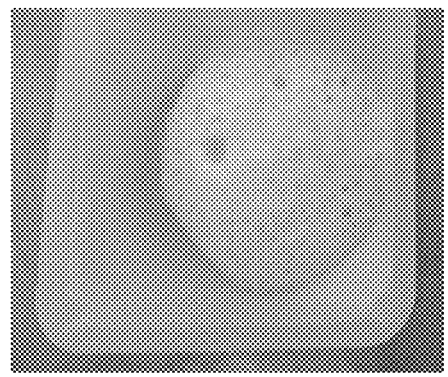
FIG. 3B is a photograph showing foam according to Comparative Example 1 one minute after being dispensed.
Figure 4A:
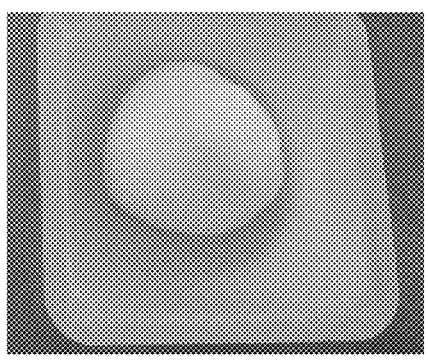
FIG. 4A is a photograph showing foam according to Example 1 two minutes after being dispensed.
Figure 4B:
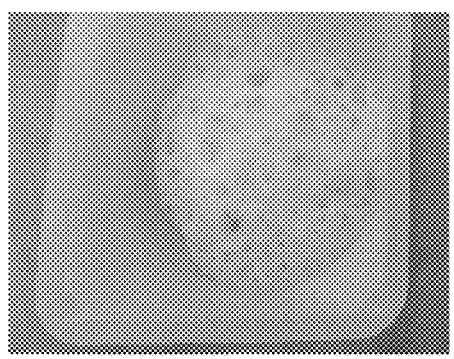
FIG. 4B is a photograph showing foam according to Comparative Example 1 two minutes after being dispensed.

As shown in FIG. 1B, the foam resulting from Comparative Example 1 was creamy with good structure immediately after being dispensed. However, in contrast with Example 1, the foam of Comparative Example 1 was unstable and began to lose structural integrity just 30 seconds after being dispensed. As shown in FIG. 2B, the dollop of foam of Comparative Example 1 began to lose its shape and flatten. Moreover, the foam began to display large bubbles, a sign of bubble coalescence and therefore foam degradation. As shown in FIGS. 3B and 4B, the foam of Comparative Example 1 exhibited continued degradation in foam viscosity at one minute and two minutes after being dispensed. The dollop of foam was almost completely flattened one minute after being dispensed. By two minutes, the foam showed numerous large bubbles and almost completely lost its shape.

What is claimed is:

1. A foaming cosmetic composition comprising:
   at least one anionic thickening agent;
   at least two alkaline compounds chosen from triethanolamine and aminomethyl propanol;
   at least one silicone; and
   at least one polyurethane latex polymer,
   wherein the weight ratio of triethanolamine to aminomethyl propane ranges from about 5:1 to about 1:5.

2. The foaming cosmetic composition according to claim 1, wherein the at least one anionic thickening agent is chosen from anionic polyurethanes, anionic guar gums, anionic acrylates copolymers, anionic polyacrylates, or mixtures thereof.

3. The foaming cosmetic composition according to claim 1, wherein the at least one anionic thickening agent is chosen from copolymers of (meth)acrylic acid, methylacrylate and dimethyl meta-isopropenyl benzyl isocyanate of ethoxylated alcohols.

4. The foaming cosmetic composition according to claim 1, wherein the total amount of anionic thickening agent ranges from about 0.01% to about 15% by weight, relative to the total weight of the composition.

5. The foaming cosmetic composition according to claim 1, wherein the at least two alkaline compounds are present in a combined amount ranging from about 0.001% to about 10% by weight, relative to the total weight of the composition.

6. The foaming cosmetic composition according to claim 1, wherein the at least two alkaline compounds are present in a combined amount ranging from about 0.2% to about 1.0% by weight, relative to the total weight of the composition.

7. The foaming cosmetic composition according to claim 1, wherein the weight ratio of triethanolamine to aminomethyl propane ranges from about 3:1 to about 1:3.

8. The foaming cosmetic composition according to claim 1, wherein the weight ratio of triethanolamine to aminomethyl propane ranges from about 2:1 to about 1:2.

9. The foaming cosmetic composition according to claim 1, wherein the at least one silicone is chosen from PEG-40/PPG-8 methylaminopropyl/hydroxypropyl dimethicone copolymers, amodimethicone/morpholinomethyl silsesquioxane copolymers, amodimethicones, or mixtures thereof.

10. The foaming cosmetic composition according to claim 1, wherein the at least one silicone is present in an amount ranging from about 0.01% to about 10% by weight, relative to the total weight of the composition.

11. The foaming cosmetic composition according to claim 1, further comprising at least one propellant.

12. The foaming cosmetic composition according to claim 1, further comprising at least one solvent chosen from water, lower monoalcohols, ethanol, isopropanol, polyols, glycols, propylene glycol, ethylene glycol, 1,3-butylene glycol, pentylene glycol, hexylene glycol, dipropylene glycol, diethylene glycol, glycerin, ethylhexyl glycerin, glycol ethers, monopropylene glycol ($C_1$-$C_4$)alkyl ethers, dipropylene glycol ($C_1$-$C_4$)alkyl ethers, tripropylene glycol ($C_1$-$C_4$)alkyl ethers, monoethylene glycol ($C_1$-$C_4$)alkyl ethers, diethylene glycol ($C_1$-$C_4$)alkyl ethers, triethylene glycol ($C_1$-$C_4$)alkyl ethers, or mixtures thereof.

13. The foaming cosmetic composition according to claim 12, wherein the total amount of the at least one solvent ranges from about 60% to about 95% by weight, relative to the total weight of the composition.

14. A method of preparing a foaming cosmetic composition comprising at least two alkaline compounds chosen from triethanolamine and aminomethyl propanol, the method comprising:
   mixing at least one anionic thickening agent and at least one silicone with at least one solvent to form a first part;
   adding a first alkaline compound to the first part and stirring to form a first neutralized composition; and
   adding a second alkaline compound to the first neutralized composition and stirring to form a foaming cosmetic composition,
   wherein the weight ratio of triethanolamine to aminomethyl propane ranges from about 5:1 to about 1:5.

15. The method according to claim 14, wherein the first alkaline compound is triethanolamine and the second alkaline compound is aminomethyl propanol.

16. The method according to claim 14, wherein:
   the at least one anionic thickening agent is chosen from anionic polyurethanes, anionic guar gums, anionic acrylates copolymers, anionic polyacrylates, or mixtures thereof;
   the first alkaline compound and the second alkaline compound are chosen from hydroxide-containing compounds chosen from alkali metal hydroxides, alkaline-earth metal hydroxides, transition metal hydroxides; ammonia; organic amines; basic amino acids, or mixtures thereof; and
   the at least one silicone is chosen from silicones, PEG-40/PPG-8 methylaminopropyl/hydroxypropyl dimethicone copolymers, amodimethicone/morpholino ethyl silsesquioxane copolymers, amodimethicones, or mixtures thereof.

17. A method of improving the stability of a foamed cosmetic composition comprising at least two alkaline compounds chosen from triethanolamine and aminomethyl propanol, the method comprising:
   mixing at least one anionic thickening agent and at least one silicone with at least one solvent to form a first part;
   adding a first alkaline compound to the first part and stirring to form a first neutralized composition;
   adding a second alkaline compound to the first neutralized composition and stirring to form a foamable cosmetic composition; and
   incorporating a gas into the foamable cosmetic composition to form a foamed cosmetic composition,
   wherein the weight ratio of triethanolamine to aminomethyl propane ranges from about 5:1 to about 1:5.

18. The method according to claim 17, wherein the first alkaline compound is triethanolamine and the second alkaline compound is aminomethyl propanol.

19. The method according to claim 17, further comprising adding a propellant to the foamable cosmetic composition, and
   dispensing the foamable cosmetic composition to form a foamed cosmetic composition.

* * * * *